United States Patent
Robertson

(10) Patent No.: US 6,216,042 B1
(45) Date of Patent: Apr. 10, 2001

(54) PACEMAKER WIRE HOLDER

(76) Inventor: Margaret P. Robertson, 28304 E. Colbern Rd., Lee's Summit, MO (US) 64063

( * ) Notice: Subject to any disclaimer, the term of this patent is extended or adjusted under 35 U.S.C. 154(b) by 0 days.

(21) Appl. No.: 09/363,613

(22) Filed: Jul. 29, 1999

(51) Int. Cl.[7] .................................................. A61N 1/00
(52) U.S. Cl. ............................................................ 607/115
(58) Field of Search ........................ 607/115; 242/588.1, 242/588.3, 590

(56) References Cited

U.S. PATENT DOCUMENTS 4,903,826 * 2/1990 Pearce ................................. 242/588.3
4,911,178 * 3/1990 Neal ................................... 242/588.1
4,978,085 * 12/1990 Letourneau ........................ 242/588.3

* cited by examiner

Primary Examiner—Scott M. Getzow
(74) Attorney, Agent, or Firm—Hovey, Williams, Timmons & Collins

(57) ABSTRACT

A holder (10) for pacemaker wires (16, 18) is provided allows convenient storage, identification and ready access to pacemaker wires and their endmost electrical contacts. The holder (10) includes a body (24) having a pair of spaced apart, elongated passageways (40, 42) each designed to receive a contact (20, 22) of the wires (16, 18), as well as side-mounted projecting elbow pairs (74, 76) adapted to receive and store convolutions of the wires (16, 18). The body (24) may be mounted via a skin adhesive (68) or a flexible neck support (72).

10 Claims, 1 Drawing Sheet

U.S. Patent    Apr. 10, 2001    US 6,216,042 B1
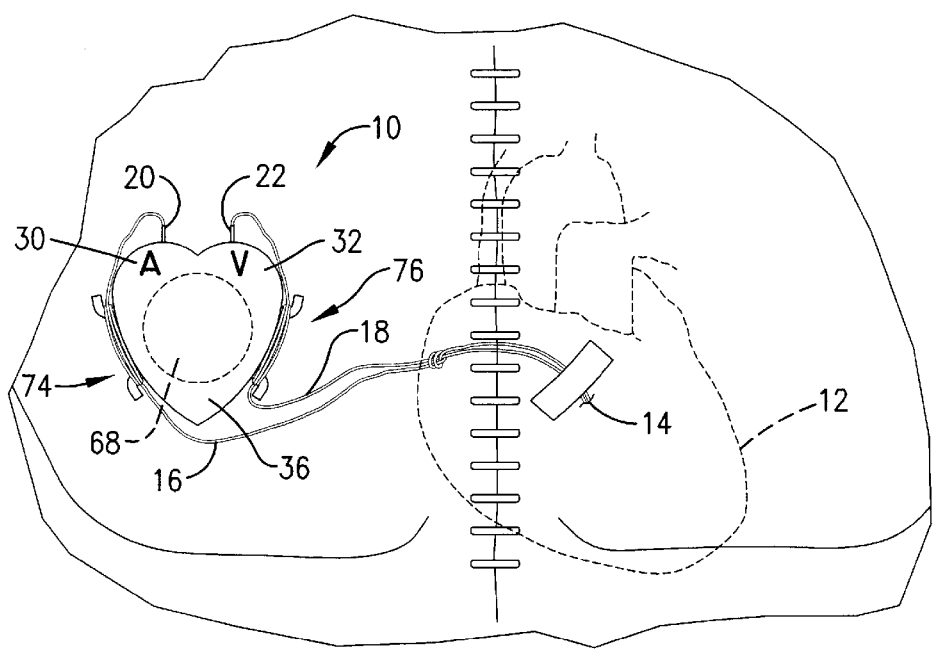
Fig. 1.
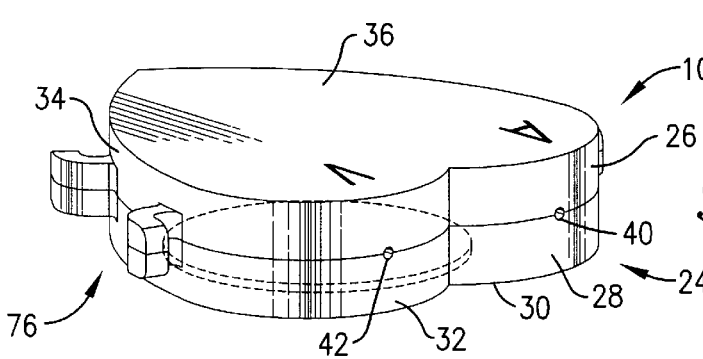
Fig. 2.
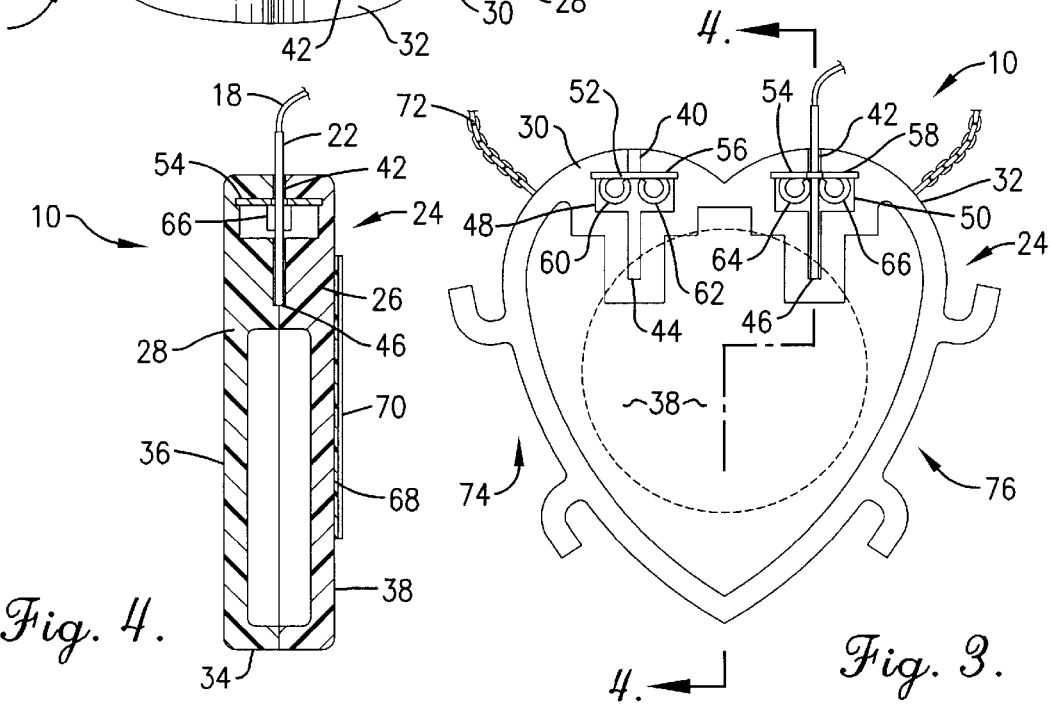
Fig. 4.
Fig. 3.

PACEMAKER WIRE HOLDER

BACKGROUND OF THE INVENTION

1. Field of the Invention

The present invention is broadly concerned with a holder for pacemaker wires often implaced in post-operative heart patients. More particularly, the invention pertains such a holder which is designed to safely and positively retain the pacemaker wires and their connection leads for easy identification and deployment thereof to allow the wires to be attached to an external pacemaker.

2. Description of the Prior Art

In many cases of heart surgery, the surgeon will attach pacemaker wires to a patient's heart. These wires pass through a skin opening, normally in the patient's chest, and are adapted to be connected as necessary to an external pacemaker. Thus, during the course of a heart patient's recuperation, it may be necessary to attach the patient to a pacemaker to in order to restart or adjust the rhythm of the patient's heart. This may be done on a regular or periodic basis and may also be required in emergency situations.

In the past, the external portions of pacemaker wires have been simply taped to the patient's chest in needle caps or gloves. This is an unsatisfactory practice because the wires can become tangled and may be difficult to identify (i.e., normally the two wires are attached to the atrium and ventricle of the heart respectively, and it is important that an attendant be able to recognize the connection site of each wire Furthermore, the conventional practice provides no assurance that the electrical contacts at the ends of the wires remain clean and readily accessible.

There is accordingly a need in the art for an improved holder or securement device for pacemaker wires which overcomes the problems associated with the improvisations of the prior art.

SUMMARY OF THE INVENTION

The present overcomes the problems outlined above, and provides an improved holder for pacemaker wires extending through a patient's skin and presenting endmost leads adapted for selective coupling with a pacemaker. The holder of the invention broadly includes a body having a pair of spaced apart lead-receiving receptacles as well as a mount coupled with the body for supporting the latter on the patient adjacent the external pacemaker wires. The receptacles are configured for releasably receiving the pacemaker wire leads while providing clear and unambiguous identification of the leads.

Preferably, the holder body is generally heart-shaped in configuration and has a pair of elongated lead-receiving passageways in the lobe sections of the body; each of the passageways is equipped with a spring-loaded resilient keeper for engaging and releasably holding a corresponding wire lead. In order to provide a positive wire lead identification, the body lobe sections are marked with an "A" and "V" to identify the atrium and ventricle leads respectively. In addition, the holder body is advantageously equipped with wire-supporting elbow pairs allowing excess pacemaker wire length to be wrapped in convolutions about the elbow pairs.

The holder body may be mounted on a patient through use of a conventional adhesive pad, or by provision of a flexible neck support or chain allowing the body to be suspended from the patient's neck.

BRIEF DESCRIPTION OF THE DRAWINGS

FIG. 1 is a fragmentary elevational view illustrating the chest of a postoperative heart patient having pacemaker wires attached to the patient's heart and extending outwardly to the patient's chest, with a pacemaker wire holder in accordance with the invention mounted on the patient's chest and supporting the outer ends of the pacemaker wires;

FIG. 2 is a perspective view of a preferred pacemaker wire holder;

FIG. 3 is an elevational view of one-half of the pacemaker wire holder illustrated in FIG. 2, and depicting the internal construction thereof; and FIG. 4 is a sectional view taken along line 4–4 of FIG. 3 and illustrating the crosssectional construction of pacemaker wire holder.

DETAILED DESCRIPTION OF THE PREFERRED EMBODIMENT

Turning now to the drawings, a pacemaker wire holder 10 is illustrated in FIGS. 2–4, with a typical use of the holder 10 depicted in FIG. 1. In particular, the holder 10 is especially designed for post-operative heart patients which have implanted pacemaker wires attached to their heart 12 and extending exteriorly through a skin opening 14 to leave elongated atrium and ventricle pacemaker wires 16 and 18. The wires 16, 18 are equipped with elongated metallic leads 20, 22 which form the terminal ends of the individual wires.

The holder 10 is preferably in the form of a synthetic resin body 24 manufactured in halves 26, 28 and adhesively or otherwise interconnected. The body 24 may be of any desired shape, but advantageously is heart-shaped, presenting a pair of lobe sections 30, 32. The half body sections 26, 28 are mirror images of each other and as best seen in FIGS. 3–4, cooperatively present a continuous sidewall 34 as well as front and rear walls 36,38. In addition, the overall body 24 has inner structure defining a pair of elongated passageways 40, 42 respectively located within each lobe section 30, 32. The passageways 40 include a lower deadend 44, 46 as best in FIGS. 3–4. In addition, the body has a compartment 48, 50 midway along the length of each corresponding passageway 40,42. A resilient keeper is mounted within each compartment 48, 50 and is preferably in the form of a metallic spring-loaded, two-part scroll spring 52, 54 presenting an uppermost plate 56, 58 as well as a pair of slightly spaced apart arcuate depending spring elements 60, 62 and 64, 66.

In use, the body 24 is supported adjacent the ends of the pacemaker wire 16, 18. In one embodiment, a mount in the form of an adhesive pad 68 affixed to the rear wall 38 and covered with a protective liner 70. In this form of the invention, the liner 70 is stripped from the pad 68 and the latter is pressed into engagement with the patient's skin in order to hold the body 24 in place. It will be appreciated that various adhesive formulations may be used in this context, for example, the adhesive used for connection of EKG pads to skin. In an alternate embodiment, a flexible neck support such as a chain 72 is attached to the body 24 so as to allow the body to be suspended from the neck of the patient.

In some cases, the pacemaker wires 16, 18 may be of substantial length. In order to most conveniently store such long wires, the body 24 is preferably equipped with two pairs of outwardly projecting elbows 74,76 respectively located on the lobe sections 30, 32. As depicted, the elbows making up each pair 74, 76 are spaced apart a distance sufficient to allow convolutions of the pacemaker wires to be wrapped thereabout.

It is important that the pacemaker wires 16, 18 be properly identified as either atrium or ventricle wires. To this end, the front wall 32 of body 24 is preferably marked with a "A" and "V" at the location of the individual passageways 40, 42. Also, it is preferred that the length of the passageways 40, 42 down to the ends 44, 46 thereof be less than the total length of the corresponding leads 20, 22. This insures that the leads can be readily removed from the associated passageways without fear of hangups.

In use, the body 24 is mounted on the patient adjacent the wire 16, 18, and the latter are wrapped around the elbow pairs 74, 76 as best illustrated in FIG. 1. The respective leads 20, 22 are then inserted into the associated passageways 40, 42, making sure that the leads are inserted in the appropriately marked "A" or "V" passageway. The leads 20, 22 are releasably retained within the passageways 40, 42 by means of the scroll springs 52, 54. As best seen in FIG. 3, the leads extend downwardly through the corresponding passageway and are resiliently engaged by the spring sections. This insures that the leads are both protected and ready for use.

In the event that pacemaker assistance is required for the patient, it is a simple matter to remove the leads from the associated passageways and unwound from the elbow pairs 74, 76 is necessary, to permit the leads 20, 22 to be attached to a pacemaker. This is of course of paramount importance if an emergency arises requiring quick connection to a pacemaker.

I claim:

1. A holder for pacemaker wires attached adjacent a patient's heart and extending through the patient's skin and presenting leads adapted for selective coupling with a pacemaker, said holder comprising:

a body having a pair of spaced apart lead-receiving receptacles; and a mount coupled with said body for supporting the body adjacent said pacemaker wires, said receptacles configured for releasably receiving said pacemaker wire leads, said body including a pair of pacemaker wire supports allowing portions of respective pacemaker wires to be stored on the body.

2. The holder of claim 1, said wire supports each comprising a pair of outwardly projecting elbows for supporting convolutions of said pacemaker wire portions.

3. The holder of claim 1, said body including identifying indicia adjacent said receptacles for identifying the lead received therein.

4. The holder of claim 1, said body being generally heart-shaped.

5. The holder of claim 4, said receptacles comprising elongated passageways formed in respective lobes of said heart-shaped body.

6. The holder of claim 1, said mount including an adhesive for securing the body to the chest of said patient.

7. The holder of claim 1, said mount including a flexible neck support secured to said body and allowing the body to be suspended from the neck of said patient.

8. A holder for pacemaker wires attached adjacent a patient's heart and extending through the patient's skin and presenting leads adapted for selective coupling with a pacemaker, said holder comprising:

a body having a pair of spaced apart lead-receiving receptacles; and a mount coupled with said body for supporting the body adjacent said pacemaker wires, said receptacles configured for releasably receiving said pacemaker wire leads, each of said receptacles comprising an elongated passageway with a resilient keeper adjacent the passageway for releasably retaining a lead within the passageway.

9. The holder of claim 8, said leads each including an elongated electrical contact section secured to the end of a corresponding pacemaker wire, said passageways having a length less than the length of a lead received therein.

10. The holder of claim 8, said keeper comprising a pair of resilient spring elements cooperatively receiving said lead.

* * * * *